US011959055B2

(12) United States Patent
Perry et al.

(10) Patent No.: US 11,959,055 B2
(45) Date of Patent: Apr. 16, 2024

(54) SYSTEMS AND METHODS FOR CONVERSION OF A BIOMASS INTO BIOFUEL USING A GEOTHERMAL HEAT SOURCE

(71) Applicant: Premium Oceanic Inc., Los Altos, CA (US)

(72) Inventors: Beau G. Perry, San Francisco, CA (US); Tracy McSheery, San Francisco, CA (US)

(*) Notice: Subject to any disclaimer, the term of this patent is extended or adjusted under 35 U.S.C. 154(b) by 0 days.

(21) Appl. No.: 17/990,032

(22) Filed: Nov. 18, 2022

(65) Prior Publication Data

US 2023/0212493 A1 Jul. 6, 2023

Related U.S. Application Data

(63) Continuation of application No. 17/570,068, filed on Jan. 6, 2022, now Pat. No. 11,505,772.

(51) Int. Cl.
| | | |
|---|---|---|
| *C12M 1/00* | (2006.01) | |
| *C12M 1/02* | (2006.01) | |
| *C12M 1/26* | (2006.01) | |

(52) U.S. Cl.
CPC ............ *C12M 21/12* (2013.01); *C12M 33/00* (2013.01); *C12M 41/18* (2013.01); *C12M 43/02* (2013.01)

(58) Field of Classification Search
CPC ...... C12M 21/12; C12M 33/10; C12M 41/18; C12M 43/02
See application file for complete search history.

(56) References Cited

U.S. PATENT DOCUMENTS

| | | |
|---|---|---|
| 8,969,030 B2 | 3/2015 | Neto |
| 9,371,549 B2 | 6/2016 | Silverman et al. |

(Continued)

FOREIGN PATENT DOCUMENTS

| | | |
|---|---|---|
| CN | 102134553 A | 7/2011 |
| CN | 110257227 A | 9/2019 |

(Continued)

OTHER PUBLICATIONS

International Search Report and Written Opinion in Application No. PCT/US2022/020529 dated Oct. 13, 2022, 9 pages.

(Continued)

*Primary Examiner* — Latosha Hines
(74) *Attorney, Agent, or Firm* — BURNS & LEVINSON, LIP; Christopher Carroll

(57) ABSTRACT

A system for converting a biomass into a biofuel including a biomass processing station arranged to receive the biomass from a biomass harvester, output the biomass to a hydrothermal liquefaction (HTL) converter, and receive a processed biomass from the HTL converter. The system includes a conduit arranged to transport the biomass from the biomass processing station to the HTL converter and transport the processed biomass from the HTL converter to the biomass processing station. The HTL converter includes a heat exchanger arranged to transfer thermal energy from a geothermal heat source to the biomass to convert the biomass into the processed biomass. The system also includes a controller arranged to monitor conditions of the biomass at locations along the conduit and adjust operations of components along the conduit to, thereby, adjust the conditions of the biomass at one or more locations along the conduit.

9 Claims, 7 Drawing Sheets

(56) References Cited

U.S. PATENT DOCUMENTS

| | | | |
|---|---|---|---|
| 9,816,035 B2 | 11/2017 | Lehoux et al. | |
| 9,970,032 B2 | 5/2018 | Silverman et al. | |
| 11,280,393 B1 | 3/2022 | Flores | |
| 2011/0247328 A1 | 10/2011 | Dubois | |
| 2014/0046105 A1 | 2/2014 | Iglesias | |
| 2014/0206912 A1* | 7/2014 | Iglesias | C10G 1/008 422/198 |
| 2017/0233678 A1 | 8/2017 | Randall et al. | |
| 2017/0342327 A1* | 11/2017 | Texier | C10J 3/82 |

FOREIGN PATENT DOCUMENTS

| | | | |
|---|---|---|---|
| EP | 2360235 A1 | 8/2011 | |
| EP | 3659431 A1 | 6/2020 | |
| FR | 2646989 A1 | 11/1990 | |
| GB | 24691998 A | 10/2010 | |
| IT | 201900000355 A1 | 7/2020 | |
| WO | WO-2006020177 A1 * | 2/2006 | B01D 53/84 |
| WO | 2013153402 A1 | 10/2013 | |
| WO | 2016123077 A1 | 8/2016 | |
| WO | 2020161711 A1 | 8/2020 | |

OTHER PUBLICATIONS

International Search Report and Written Opinion in Application No. PCT/US2022/020530 dated Oct. 13, 2022, 10 pages.

International Search Report and Written Opinion in Application No. PCT/US2023/010171 dated Apr. 14, 2023, 14 pages.

Carr et al., "Utilizing geothermal heat for hydrothermal liquefaction of algae," USDOE Office of Science, pp. 1-31, DOI:10.2172/1242689 [online] URL: https://www.osti.gov.servlets/purl/124689/ [retrieved on Apr. 4, 2023], (Mar. 21, 2016) 31 pages.

Reddy et al., "ASI: Hydrothermal extraction and characterization of bio-crude oils from wet chlorella sorokiniana and dunaliella tertiolecta," Environmental Progress & Sustainable Energy, vol. 32, No. 4, pp. 910-915, DOI:10.1002/ep. 11862 (Dec. 1, 2013), 6 pages.

* cited by examiner

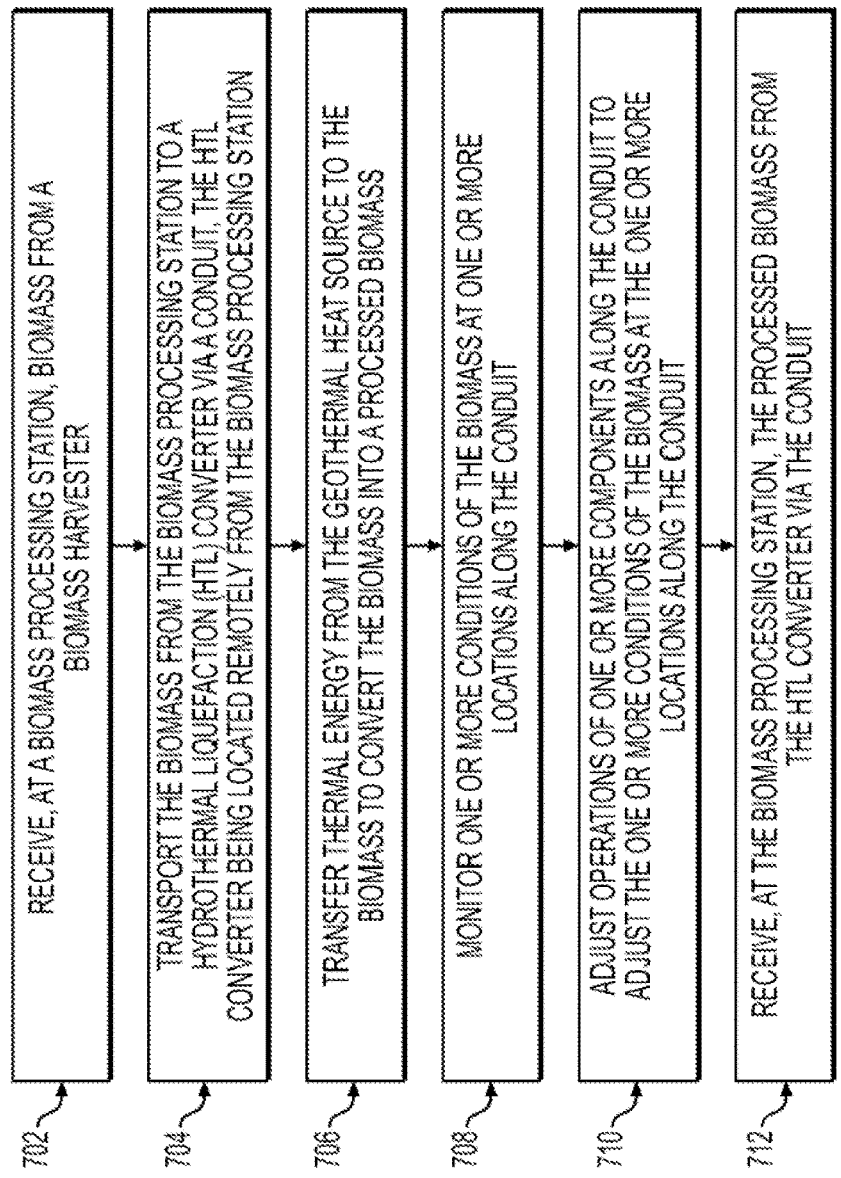

SYSTEMS AND METHODS FOR CONVERSION OF A BIOMASS INTO BIOFUEL USING A GEOTHERMAL HEAT SOURCE

REFERENCE TO RELATED APPLICATIONS

This application is a continuation of U.S. patent application Ser. No. 17/570,068, filed on Jan. 6, 2022, which issued as U.S. Pat. No. 11,505,772, the entire contents of the which are incorporated herein by reference.

TECHNICAL FIELD

This application relates generally to converting a biomass into a biofuel and, more particularly, to geothermal biofuel production based on algae or seaweed.

BACKGROUND

Fuel derived from algae, often referred to as the 'third-generation biofuel', provides advantages over earlier biofuels based on plant crops including sugar cane and corn (e.g., the "first generation of biofuel") and vegetable or animal waste streams (e.g., the "second generation of biofuel").

Algae biofuels have advantages that include higher biofuel yields compared to previous systems, a diverse set of possible fuel types including biodiesel, butanol, ethanol and jet fuel, as well as the capability to deploy large-scale algae cultivation in open ponds or more advanced closed-loop systems. Biofuel production from algae can be done on land unsuitable for food crops, removing concerns that algae biofuel feedstock crops would compete with food producers.

Algae-based biofuel companies have unsuccessfully attempted to chemically engineer algae capable of scaling up to produce tens of millions of gallons of fuel at prices competitive with fossil fuels. Fuel conversion from algae has been generally based on the feedstock's high concentrations of lipids, i.e., fatty, oil-containing acid molecules that can be extracted to create biofuels. Algae can be converted into various types of fuels, depending on the technique and the part of the cells used. The lipid, or oily part of the algae biomass can be extracted and converted into biodiesel through a process similar to that used for any other vegetable oil or converted in a refinery as a replacement for petroleum-based fuels. Alternatively, or following lipid extraction, the carbohydrate content of algae can be fermented into bioethanol or butanol fuel.

Biofuel is typically produced from algae via dehydration or hydrothermal liquefaction. Hydrothermal liquefaction implements a continuous process that subjects harvested wet algae to high temperatures and pressures, e.g., 350° C. (662° F.) and 3,000 pounds per square inch (21.000 kPa). Unfortunately, the cost of generating such high temperatures and pressures has traditionally exceeded the value of the resulting algae-based biofuel product. Such products include crude oil, which can be further refined into aviation fuel, gasoline, or diesel fuel using one or many upgrading processes. Other outputs from the conversion process can include clean water, gas fuel or nutrients such as nitrogen, phosphorus, and potassium.

Despite significant efforts to develop cost-efficient and scalable conversion processes, practical biofuel production systems have yet to be achieved. Technical problems remain in relation to the energy balance of lipid extraction, maintaining suitable growing conditions in open waters, power consumption, and the immense volumes of water, $CO_2$ and fertilizer required to allow the algae to photosynthesize fast enough in large volumes.

While there have been many research efforts to develop algae biofuel production systems, none of the existing production efforts have been capable of converting algae into biofuel in a sufficiently scalable and cost-efficient manner.

SUMMARY

The application, in various implementations, addresses deficiencies associated with converting a biomass such as algae into a biofuel.

Systems and methods described herein utilize a geothermal energy source within an ocean and/or under the Earth to enable an efficient hydrothermal liquefaction (HTL) process for thermochemical conversion of wet algae and/or microalgae to produce a liquid energy carrier referred to 'bio oil,' "biofuel," or 'biocrude', along with gaseous, aqueous and/or solid by-products.

In one aspect, a system for converting a biomass into a biofuel includes a biomass processing station arranged to: receive the biomass from a biomass harvester, output the biomass to a hydrothermal liquefaction (HTL) converter, and receive a processed biomass from the HTL converter. The system includes a conduit arranged to transport the biomass from the biomass processing station to the HTL converter and transport the processed biomass from the HTL converter to the biomass processing station. The HTL converter includes a heat exchanger arranged to transfer thermal energy from a geothermal heat source to the biomass to convert the biomass into the processed biomass. The system further includes a controller arranged to monitor one or more conditions of the biomass at the one or more locations along the conduit and adjust operations of one or more components along the conduit to, thereby, adjust the one or more conditions of the biomass at the one or more locations along the conduit.

In one implementation, the system includes one or more sensors located at one or more sections of the conduit that enable the controller to monitor the one or more conditions of the biomass by receiving sensor data associated with one or more conditions of the biomass from the one or more sensors. The biomass may include an algae and the processed biomass may include bio oil, biocrude, and/or biofuel. In certain configurations, converting the biomass into a processed biomass includes depolymerization of the biomass to bio oil. The controller may be arranged to adjust the operations of the one or more components to optimize the one or more conditions of the biomass to optimize a quality and/or yield of the processed biomass. The one or more components may include at least one of a pump and a flow control valve. The one or more conditions of the biomass may include temperature, rate of temperature change, pressure, flow rate, catalyst concentration, and/or residence time within the HTL converter.

The geothermal heat source may include a volcano, volcanic vent, and/or a hydrothermal vent. The HTL converter may resides within a body of water and a substantial portion of the conduit may be surrounded by the body of water. The biomass processing station and biomass harvester may be in proximity with each other within the body of water.

In another aspect, a method for converting a biomass into a biofuel includes: receiving, at a biomass processing station, the biomass from a biomass harvester; transporting the biomass from the biomass processing station to a hydrothermal liquefaction (HTL) converter via a conduit, where the HTL converter is located remotely from the biomass processing station and within proximity to a geothermal heat source; transferring thermal energy from the geothermal heat source to the biomass to convert the biomass into a processed biomass; monitoring one or more conditions of the biomass at one or more locations along the conduit; adjusting operations of one or more components along the conduit to adjust the one or more conditions of the biomass at the one or more locations along the conduit; and receiving, at the biomass processing station, the processed biomass from the HTL converter via the conduit.

In a further aspect, a system for converting a biomass into a biofuel includes a biomass processing station arranged to: receive the biomass from a biomass harvester, output the biomass to a HTL converter, and receive a processed biomass from the HTL converter. The system includes a first conduit arranged to transport the biomass from the biomass processing station to the HTL converter and transport the processed biomass from the HTL converter to the biomass processing station. The HTL converter includes a first heat exchanger arranged to transfer thermal energy from a superheated fluid to the biomass to convert the biomass into the processed biomass. The system includes a second conduit arranged to transport the superheated fluid to the HTL converter from a second heat exchanger in proximity to a geothermal heat source. The second heat exchanger is arranged to transfer thermal energy from the geothermal heat source to the superheated fluid. The system further includes a controller arranged to perform at least one of i) monitor one or more conditions of the biomass at the one or more locations along the first conduit and adjust operations of one or more components along the first conduit to, thereby, adjust the one or more conditions of the biomass at the one or more locations along the first conduit, and ii) monitor one or more conditions of the superheated fluid at one or more locations along the second conduit and adjust operations of one or more components along the second conduit to, thereby, adjust the one or more conditions of the superheated fluid at the one or more locations along the second conduit.

Any two or more of the features described in this specification, including in this summary section, may be combined to form implementations not specifically described in this specification. Furthermore, while this specification may refer to examples of systems, methods, and devices related algae or seaweed producing bioreactors, such techniques also apply equally to bioreactors arranged to cultivate other organisms or products.

The systems and methods described herein are capable of refining any biomass including terrestrial ones, and also plastic waste as a fraction of the feedstock. In some implementations, the primary outputs of the systems and methods include Biocrude, biofuels and hydrogen. In the case of hydrogen, implementations described herein can yield a set of carbon compound byproducts that can be sequestered or have applications in, for example, concrete and other industrial materials. Hence, as a platform or process, the systems and methods described herein have the potential to be a carbon-negative solution for Bioenergy with Carbon Capture and Storage (BECCS), based on a lack of emissions as a refining system. The systems and methods described herein, in various implementations, can also, depending on what material is being processed, produce nitrogen, phosphorous, and other valuable material byproducts including, in some cases, rare earth metals such as Scandium, or a range of other rare earth elements (REEs). Paltry percentage, but if we process 1M tons a day these become notable. Other applications of the systems and methods described herein may render materials for a material market, e.g., bioplastics. With a capacity to accept waste plastics along with biomass, the geothermal and/or hydrothermal liquefaction systems and methods described herein can also serves as a recycling solution. A geothermal HTL (GeoHTL) refinery such as described with respect to the systems and methods herein can also be deployed on land, on an ocean surface, or on the ocean floor.

The details of one or more implementations are set forth in the accompanying drawings and the following description. Other features and advantages will be apparent from the description and drawings, and from the claims.

DESCRIPTION OF THE DRAWINGS

FIG. 7 shows a process for converting a biomass into biofuel using a geothermal heat source.

Like reference numerals in different figures indicate like elements.

DETAILED DESCRIPTION

The application, in various implementations, addresses deficiencies associated with converting a biomass, such as algae, into a biofuel. This application describes exemplary systems, methods, and devices that effectively and efficiently implement biomass conversion to biofuel by using a geothermal heat source to enable depolymerization of the biomass to bio oil. The conversion process may be enhanced by controlling conditions associated with the biomass during conversion including controlling temperature, rate of temperature change, pressure, catalyst concentration, and/or flow rate of the biomass through an HTL converter to, thereby, optimize production yield of the bio oil and/or biofuel derived from the conversion. The optimization may be further enhanced by monitoring conditions of the biomass and/or bio oil along a conduit transporting the materials to and from the HTL converter using sensors to provide sensor data to a controller that uses AI and/or ML to process the sensor data and dynamically adjust operations of various conversion system components to adjust one or more conditions within the conduit and/or HTL converter, which optimizes biofuel quality and/or yield, or optimizes biofuel characteristics for a particular use.

Figure 1:
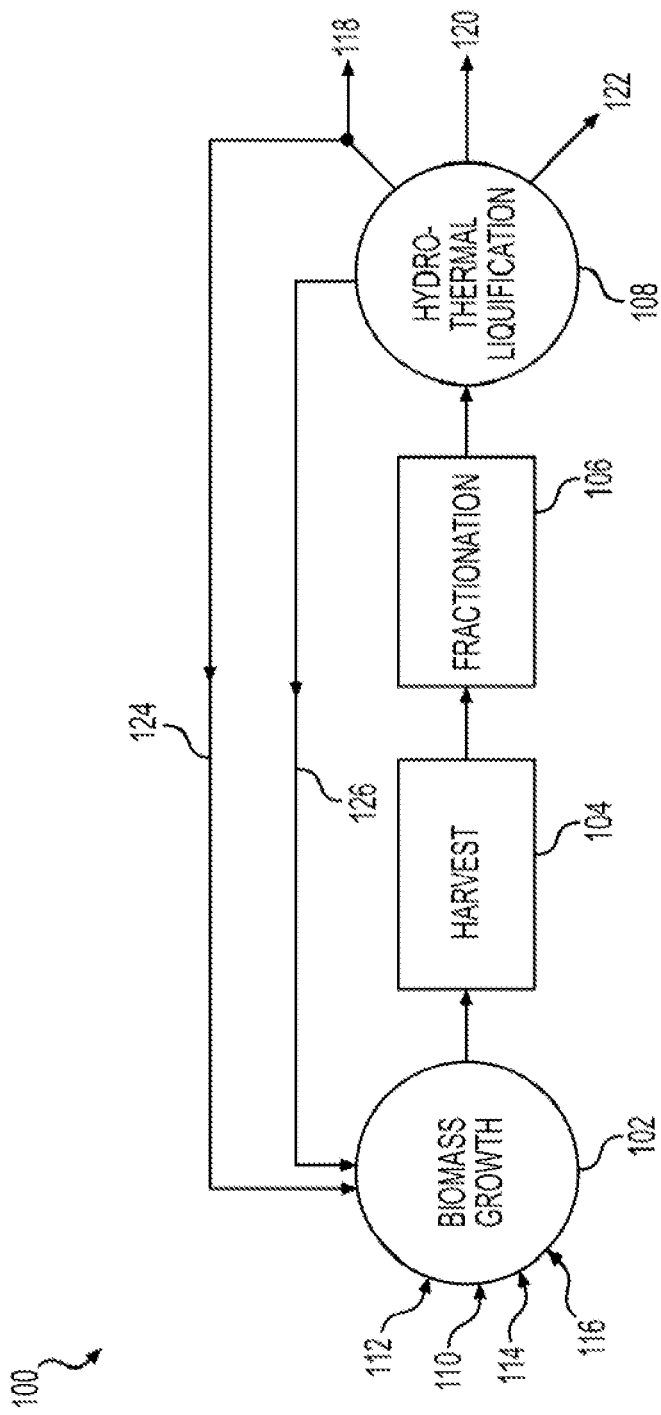
FIG. 1 is a diagram of an exemplary biomass to biofuel conversion process.

FIG. 1 is a diagram of an exemplary biomass to biofuel conversion process 100. The conversion process 100 includes a biomass growth stage 102, harvesting stage 104, fracturing stage 106, and a hydrothermal liquefaction (HTL) stage 108. During biomass growth stage 102, a carbon source (e.g., algae seed) 110 is combined at least with light 112, water 114, and nutrients 116 to facilitate growth of a biomass (e.g., algae) within, for example, a photobioreactor. Detailed descriptions of on-shore, closed loop, open, and deepwater photobioreactors are provided in U.S. Provisional Patent Application No. 63/172,407, entitled "Photobioreactor Systems and Methods," U.S. patent application Ser. No. 17/564,779, filed on Dec. 29, 2021, entitled "Photobioreactor Systems and Methods," and U.S. patent application Ser. No. 17/564,814, filed on Dec. 29, 2021, entitled "Systems and Methods for Deepwater Photobioreactor," the entire contents of which are incorporated herein by reference.

Once the biomass is formed during the growth stage 102, the biomass is harvested from, for example, a photobioreactor. During harvesting, the harvested biomass may be further fractioned via a fractionation stage 106 to reduce the size of the biomass materials. The biomass is then depolymerized during HTL stage 108 into bio oil or biofuel. By products of the HTL stage 108 may include CO2 rich gas that can be returned to the biomass growth stage 102 via feedback 124 to enhance the biomass growth process. Other materials such as water and nutrients may be recycled back via a feedback 126 to biomass growth stage 102 for more efficient biofuel production. Solid residue 120 including, for example, char may be extracted from the biofuel during stage 108. Bio crude 122, biofuel, and/or bio oil are also extracted for storage, use, or further processing as a fuel.

Figure 2:
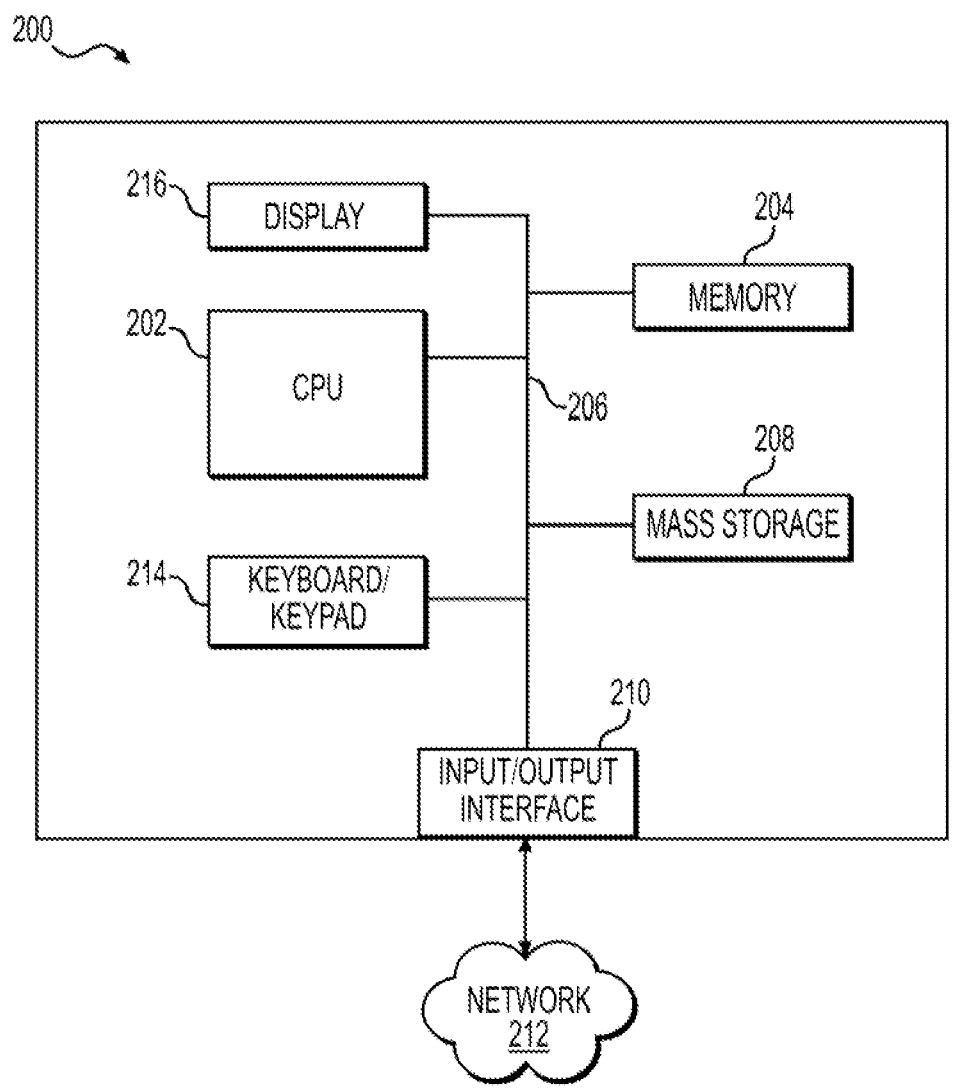
FIG. 2 shows a diagram of a computer system for a controller arranged to control operations of a biomass to biofuel conversion system.

FIG. 2 includes a block diagram of a computer system 200 for performing the functions of a computer such as for the controller of FIGS. 3,4, 5, and 6. The exemplary computer system 200 includes a central processing unit (CPU) 202, a memory 204, and an interconnect bus 206. The CPU 202 may include a single microprocessor or a plurality of microprocessors for configuring computer system 200 as a multiprocessor system. The memory 204 illustratively includes a main memory and a read only memory. The computer 200 also includes the mass storage device 208 having, for example, various disk drives, tape drives, etc. The main memory 204 also includes dynamic random access memory (DRAM) and high-speed cache memory. In operation, the main memory 204 stores at least portions of instructions and data for execution by the CPU 202.

The mass storage 208 may include one or more magnetic disk or tape drives or optical disk drives or solid state memory, for storing data and instructions for use by the CPU 202. At least one component of the mass storage system 208, preferably in the form of a disk drive, solid state, or tape drive, stores the database used for processing sensor data from sensor array 116 and running AI and/or ML engines and/or neural networks for controlling biofuel conversion systems 300, 400, and 500. The AI and/or ML engines may implement ANNs and/or Deep-learning architectures such as deep neural networks, deep belief networks, recurrent neural networks and convolutional neural networks to dynamically adjust environmental conditions within the conduits, HTL converter, or other components of systems 300, 400, 500. To effect automated control of system 300, 400, 500, and 600, computer 200 may send control signals to various components 322, 324, 326, 424, 426, 428, 524, 526, and 528 of systems 300, 400, 500, or components of system 600, to either, open, close, turn on, turn off, adjust flow rate, adjust mixing rate, and cooling rate, to optimize bio crude and/or biofuel production within the HTL converter of system 300, 400, 500, or 600. The mass storage system 208 may also include one or more drives for various portable media, such as a floppy disk, flash drive, a compact disc read only memory (CD-ROM, DVD, CD-RW, and variants), memory stick, or an integrated circuit non-volatile memory adapter (i.e. PC-MCIA adapter) to input an d output data and code to and from the computer system 200. In some implementations, computer 200 and/or controller 118 may control multiple bioreactors concurrently via a data network such as network 212. Controller 118 may coordinate operations among the multiple bioreactors to optimize output production and/or yield among the multiple bioreactors. Network 212 may include a wireless, Adhoc, and/or mobile network, supporting multiple computing server implementations in a cloud computing environment. Various environmental sensors and/or multiple biofuel conversion systems, harvesters (e.g., photobioreactors), and biomass processing stations, and/or robots servicing component of these systems may be communicatively connected via network 212 as, for example, Internet-of-Things (IoT) capable systems and/or devices. In some implementations, network 212 may enable computer 200 and/or controller 118 to coordinate operations of multiple photobioreactors by using predictive analytics to process, for example, global position system (GPS) data and other big data to coordinate operations and control of multiple concurrently operating bioreactors over a geographic area. In certain implementations, network 212 may enable collections of, for example, GPS data from multiple bioreactors and use an ML program to enhance security and/or performance for biofuel production on land or in the sea.

The computer system 200 may also include one or more input/output interfaces for communications, shown by way of example, as interface 210 and/or transceiver for data communications via the network 212. The data interface 210 may be a modem, an Ethernet card or any other suitable data communications device. To provide the functions of a computer 102, the data interface 210 may provide a relatively high-speed link to a network 212, such as an intranet, or the Internet, either directly or through another external interface. The communication link to the network 212 may be, for example, optical, wired, or wireless (e.g., via satellite or cellular network). Alternatively, the computer system 200 may include a mainframe or other type of host computer system capable of Web-based communications via the network 212. The computer system 200 may include software for operating a network application such as a web server and/or web client.

The computer system 200 may also include suitable input/output ports, that may interface with a portable data storage device, or use the interconnect bus 206 for interconnection with a local display 216 and keyboard 214 or the like serving as a local user interface for programming and/or data retrieval purposes. The display 216 and/or display 120 may include a touch screen capability to enable users to interface with the system 200 by touching portions of the surface of the display 216. Remote operations personnel may interact with the system 200 for controlling and/or programming the system from remote terminal devices via the network 212.

The computer system 200 may run a variety of application programs and store associated data in a database of mass storage system 208. One or more such applications may include a biofuel conversion controller 344, 450, 550, and 612 that controls various components of system 300, 400, 500, and 600 during the biofuel conversion process.

The components contained in the computer system 200 may enable the computer system to be used as a server, workstation, personal computer, network terminal, mobile computing device, and the like. As discussed above, the computer system 200 may include one or more applications that enable cleaning and sanitization of a footwear sole or soles. The system 200 may include software and/or hardware that implements a web server application. The web server application may include software such as HTML, XML, WML, SGML, PHP (Hypertext Preprocessor), CGI, and like languages.

The foregoing features of the disclosure may be realized as a software component operating in the system 200 where the system 200 includes UNIX workstation, a Windows workstation, a LINUX workstation, or other type of workstation. Other operating systems may be employed such as, without limitation, Windows, MAC OS, and LINUX. In some aspects, the software can optionally be implemented as a C language computer program, or a computer program written in any high level language including, without limitation, JavaScript, Java, CSS, Python, PHP, Ruby, C++, C, Shell, C#, Objective-C, Go, R, TeX, VimL, Per, Scala, CoffeeScript, Emacs Lisp, Swift, Fortran, or Visual BASIC. Certain script-based programs may be employed such as XML, WML, PHP, and so on. The system 200 may use a digital signal processor (DSP).

As stated previously, the mass storage 208 may include a database. The database may be any suitable database system, including the commercially available Microsoft Access database, and can be a local or distributed database system. A database system may implement Sybase and/or an SQL Server. The database may be supported by any suitable persistent data memory, such as a hard disk drive, RAID system, tape drive system, floppy diskette, or any other suitable system. The system 200 may include a database that is integrated with the system 200, however, it is understood that, in other implementations, the database and mass storage 208 can be an external element.

In certain implementations, the system 200 may include an Internet browser program and/or to be configured to operate as a web server. In some configurations, the client and/or web server may be configured to recognize and interpret various network protocols that may be used by a client or server program. Commonly used protocols include Hypertext Transfer Protocol (HTTP), File Transfer Protocol (FTP), Telnet, and Secure Sockets Layer (SSL), and Transport Layer Security (TLS), for example. However, new protocols and revisions of existing protocols may be frequently introduced. Thus, to support a new or revised protocol, a new revision of the server and/or client application may be continuously developed and released.

The computer system 200 may include a web server running a Web 2.0 application or the like. Web applications running on system 200 may use server-side dynamic content generation mechanisms such, without limitation, Java servlets, CGI, PHP, or ASP. In certain embodiments, mashed content may be generated by a web browser running, for example, client-side scripting including, without limitation, JavaScript and/or applets on a wireless device.

In certain implementations, system 200 and/or controller 118 may include applications that employ asynchronous JavaScript+XML (Ajax) and like technologies that use asynchronous loading and content presentation techniques. These techniques may include, without limitation, XHTML and CSS for style presentation, document object model (DOM) API exposed by a web browser, asynchronous data exchange of XML data, and web browser side scripting, e.g., JavaScript. Certain web-based applications and services may utilize web protocols including, without limitation, the services-orientated access protocol (SOAP) and representational state transfer (REST). REST may utilize HTTP with XML.

The system 200 may also provide enhanced security and data encryption. Enhanced security may include access control, biometric authentication, cryptographic authentication, message integrity checking, encryption, digital rights management services, and/or other like security services. The security may include protocols such as IPSEC and IKE. The encryption may include, without limitation, DES, 3DES, AES, RSA, and any like public key or private key based schemes.

Figure 3:
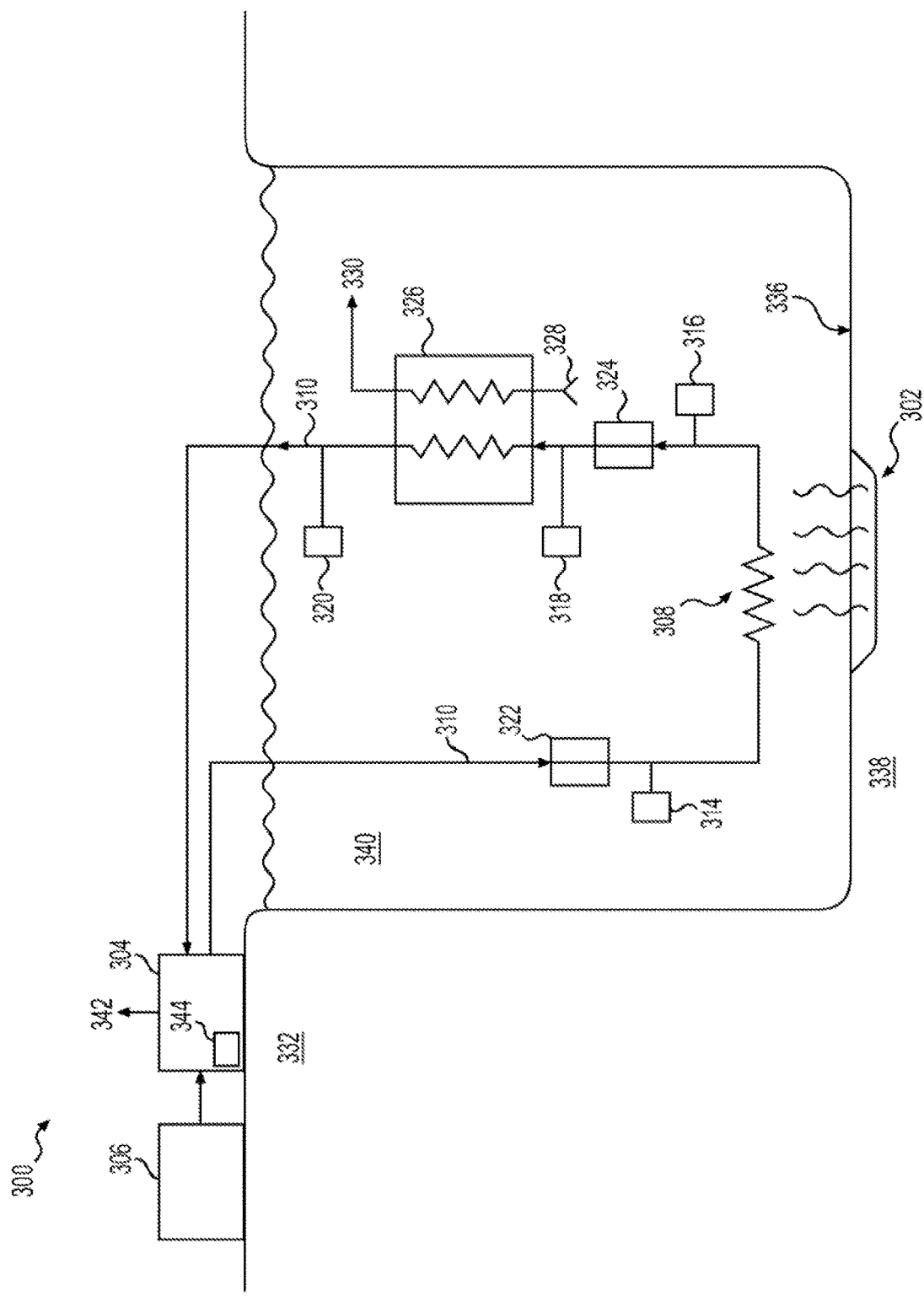
FIG. 3 shows a system for converting a biomass into biofuel using a geothermal heat source.

FIG. 3 shows a system 300 for converting a biomass into biofuel using a geothermal heat source 302. System 300 includes a biomass processing station 304 arranged to receive the biomass from a biomass harvester 306 and then output the biomass to a HTL converter 308. The processing station 304 also receives a processed biomass from the HTL converter 308. The system 300 uses a conduit 310 to transport the biomass from the biomass processing station 304 to the HTL converter 308 and transport the processed biomass from the HTL converter 308 to the biomass processing station 304. HTL converter 308 includes a heat exchanger arranged to transfer thermal energy from geothermal heat source 302 to the biomass being transported through conduit 310 to convert the biomass into the processed biomass. System 300 also includes a controller 344 that is arranged to monitor one or more conditions of the biomass via sensors 314, 316, 318, and 320 at the one or more locations along the conduit 310 and adjust operations of one or more components 322, 324, and 326 along the conduit 310 to, thereby, adjust the one or more conditions of the biomass at the one or more locations along the conduit 310.

The conditions monitored by sensors 314-320 may include, without limitation, temperature, rate of temperature change, pressure, flow rate, catalyst concentration, and/or residence time the biomass within HTL converter 308. Controller 344 may monitor the one or more conditions of the biomass by receiving sensor data associated with one or more conditions of the biomass from one or more of sensors 314-320. The biomass may include an algae while the processed biomass may include bio oil, bio crude, and/or biofuel. The conversion of the biomass to biofuel may include depolymerization of the biomass to bio oil.

In various implementations, controller 344 is configured to adjust the operations of one or more of components 322, 324, and 326 to optimize conditions of the biomass and, thereby, optimize a quality and/or yield of the processed biomass. Components 322 and 324 may include flow regulators such as, for example, a pump and/or a flow control valve. A pump may be a variable speed pump to adjust flow rate within conduit 310. A flow control valve may be adjustable to adjust flow rate with conduit 310. Heat exchanger 326 may be controlled by controller 344 to regulate an output temperature of from heat exchanger 326 before the processed biomass, e.g., biofuel, is returned to processing station 304. Heat exchanger 326 may receive cooling water at a temperature set by the depth of water inlet 328 and pass water through to extract heat from the processed biomass also passing through heat exchanger 326 via conduit 310. The flow rate of cooling water through heat exchanger 326 may be regulated by a flow regulator controlled by controller 344. The heated cooling water is then expelled into the surround body of water 340, e.g., the ocean. In this way, the temperature of the processed biomass is reduced before handling at processing station 304. Although not shown in FIG. 3, controller 344 is in electrical communications, e.g., via electrical conduits, with sensors 314-320 and components 322-326 to enable electrical communications associated with controlling conditions of the biomass in system 300.

The geothermal heat source 302 may include, without limitation, a volcano, volcanic vent, or a hydrothermal vent. Although HTL converter 308 is shown adjacent to geothermal heat source 302, HTL converter 308 may extend through source 302 within the earth 338 below the ocean floor 336. HTL converter 308 may include a section of conduit 310 that extends through and/or near source 302. The location of HTL converter 308 with respect to source 302 may depend on the desired amount of heat exchange and temperature needed to convert the biomass into a processed biomass. HTL converter 308 may include a single pipe (i.e., section of conduit 310) that extends through a region of the geothermal heat source 302. The pipe may be substantial straight, U-shaped, serpentine, and/or curved in portions. HTL converter 308 may include multiple parallel pipes and/or capillaries with a common inlet and outlet that interface with conduit 310.

As illustrated in FIG. 3, HTL converter 308 may reside within a body of water 340 such as the ocean where a substantial portion of conduit 310 is surrounded by the body of water 340. While FIG. 3 shows the harvester 306 and biomass processing station 304 on land 322, the biomass processing station 304 and biomass harvester 306 may reside in proximity with each other within the body of water 340. The biomass processing station 304 may be located on a vessel, rig, or platform on the body of water 340. The harvester 306 may include one or more photobioreactors or deepwater photobioreactors in the body of water 340 and in proximity to the system 300 and/or station 304. The harvester 306 may be less than or equal to about 5 miles (about 8 Km), 3 miles (about 4.8 Km), 1 mile (about 1.6 Km), 0.5 miles (about 0.8 Km), 0.25 miles (about 0.4 Km) from system 300 and/or biomass processing station 304.

In certain implementations, controller 344 is arranged to enable automated control of components 322, 324, and 326 of the biofuel conversion system 300. Controller 344 may include a processor running artificial intelligence (AI) and/or machine learning (ML), neural networks, Bayesian networks, and/or fuzzy logic to process sensor data received from one or more of sensors 314-316 and control various biomass parameters of system 300 including, without limitation, biomass flow rates, temperature, rate of temperature change, nutrient concentrations, pH levels, dissolved gases concentrations, and/or residence time within HTL converter 308. Controller 344 may implement Artificial Neural Networks (ANN) and/or Deep-learning architectures such as deep neural networks, deep belief networks, recurrent neural networks and convolutional neural networks to dynamically adjust biomass and/or conduit 310 conditions within system 300, 400, 500, and 600. Controller 344 may implement supervised learning, reinforcement learning, and/or unsupervised learning. Reinforced learning may include game theory, control theory, operations research, information theory, and/or simulation-based optimization to dynamically adjust biomass and/or conduit 310 conditions within system 300, 400, 500, and 600. The system 300 cultivation and/or conversion environment may be represented as a Markov decision process (MDP). Controller 344 may create multiple decision trees that solve multiple conversion optimization problems. Controller 344 may use Bayesian networks to optimize an biomass to biofuel conversion process.

Controller 344 may use one or more neural networks, such multilayer perceptrons (MLPs), convolutional neural networks (CNNs), or deep Boltzman machines (DBM) that are trained to compute a function that maps an input vector to an output vector. The N-element output vector may convey estimates of the probabilities of N biomass conversion settings. In some implementations, controller 344 uses a recurrent neural network (RNN) where its neurons send feedback signals to each other to enable dynamic temporal behavior. Controller 344 may use an enhanced RNN referred to as long short-term memory (LSTM) and/or hierarchal temporal memory (HTM). Controller 344 may use a combination of the aforementioned AI algorithms to form a hybrid control system. A decision tree is a generic term that describes a decision process that may use one or more attributes at each node and/or use an information theoretic measure to formulate queries at each node to reach a decision on the optimal biomass conversion configuration for producing biofuel using system 300, 400, 500, or 600.

In operation in some implementations, the biomass processing station 304 receives the biomass from biomass harvester 306. Conduit 310 transports the biomass from the biomass processing station 304 to HTL converter 308 that is located remotely from the biomass processing station 304 and within proximity to geothermal heat source 302. One or more pumps within processing station 304, flow regulator 322, and or flow regulator 324 may be operated to facilitate transport of the biomass through conduit 310. At HTL converter 308, thermal energy is transferred from geothermal heat source 302 to the biomass, resulting in a conversion of the biomass into a processed biomass, e.g., bio crude. Controller 344 may monitor one or more conditions of the biomass at one or more locations along the conduit 310 via sensors 314-320 and, in response to sensor data received from one or more of sensors 314-320, adjust operations of one or more components 322, 324, and 326 along the conduit 310 to adjust the one or more conditions of the biomass at the one or more locations along the conduit 310. Then, the processed biomass from the HTL converter 308 is received at the biomass processing station 304 via conduit 310. The processed biomass may then be outputted from the biomass processing station via outlet 342 to a storage facility or further processing facility. Biomass processing station may include or be part of a fuel refinery.

Hydrothermal liquefaction (HTL) is a thermal depolymerization process that is used to convert a wet biomass, and other macromolecules, into crude oil under moderate to high temperature and high pressure. The crude oil may have a high energy density with a lower heating value of, for example, 33.8-36.9 MJ/kg and 5-20 weight (wt) % of oxygen and renewable chemicals. The reaction may include homogeneous and/or heterogeneous catalysts to enhance product quality and yields. The carbon and hydrogen of an organic material, such as the biomass, can be thermochemically converted into hydrophobic compounds with low viscosity and high solubility. Depending on the processing conditions, the biofuel can be used for heavy engines, including marine and rail or upgraded to transportation fuels, such as diesel, gasoline or jet-fuels.

In a hydrothermal liquefaction process, long carbon chain molecules in a biomass are thermally cracked and oxygen is removed in the form of $H_2O$ (dehydration) and $CO_2$ (decarboxylation). These reactions result in the production of a high H/C ratio bio-oil where H/C=(wt % hydrogen/atomic wt hydrogen)/(wt % carbon/atomic wt carbon). Typical implementations of hydrothermal liquefaction operate at temperatures between 250-550° C. and high pressures of 5-25 MPa while subjected to catalysts for 20 to 60 minutes. But, in certain implementations, controller 344 may regulate higher or lower temperatures within HTL converter 308 and/or conduit 310 to optimize gas or liquid yields of the processed biomass. At these temperatures and pressures, the water present in the biomass may become either subcritical or supercritical, depending on the conditions, and may act as a solvent, reactant, and catalyst to facilitate the reaction of the biomass to a processed biomass, e.g., a bio oil.

Controller 344, 450, 550, and 612 may control the conversion parameters of the biomass to bio oil based on controlling one or more of various conditions including: feedstock composition, temperature and heating rate, pressure, flow rate, solvent composition, residence time in the HTL converter 308, and the composition of catalysts. In some configurations, controller 344 may control residence time in HTL converter 308 by controlling the biomass flow rate through HTL converter 308. For example, if the conduit 310 length of HTL converter 308 is 200 meters, the controller 344 may set operations of, for example, flow regulator 322 to set the biomass flow rate through HTL converter 308 to 10 m/min. This would result in biomass residence time within HTL converter of 20 minutes which is equal to the distance of 200 meters divided by the flow rate (10 m/min). Residence times of the biomass within the HTL converter 308 may be less than or equal to about 60 minutes, 40 minutes, 20 minutes, 10 minutes, 5 minutes, and 1 minute. Controller 344 may adjust the residence time based on the reaction conditions such as, without limitation, feedstock, solvent ratio and temperature, and so on. In certain implementations, optimization of the residence time enables a complete depolymerization of the biomass without allowing further reactions to occur.

The temperature of the reaction within HTL converter 308 determines the depolymerization of the biomass to bio-oil, along with the repolymerization of the biomass into char. While the ideal reaction temperature is dependent on the feedstock used, temperatures above ideal can lead to an increase in char formation and eventually increased gas formation, while lower than ideal temperatures reduce depolymerization and overall product yields. In various implementations, controller 344 automatically determines the optimal conditions for producing an optimal biofuel quality and/or yield.

Controller 344 may also control the rate of heating of the biomass in the HTL converter 308 to potentially control the effects of secondary reactions that may become dominant where heating rates that are too low, which may lead to the formation of char. While high heating rates may be required to form liquid bio oil, controller 344 may set a threshold heating rate and temperature where liquid production is inhibited while gas production is favored in secondary reactions. Controller 344 may regulate pressure with temperature to determine the super or subcritical state of solvents, the overall reaction kinetics, and/or the energy inputs required to produce the desired processed biomass, e.g., biofuel.

While water acts as a catalyst in the HTL reaction, other catalysts can be added to the HTL converter 308 and/or conduit 310 to optimize the biomass to biofuel conversion. System 300 may include catalysts having water-soluble inorganic compounds and salts, including KOH and Na2CO3, and/or transition metal catalysts using Ni, Pd, Pt, and Ru supported on either carbon, silica or alumina within the HTL converter 308 and/or conduit 310. The addition of these catalysts can increase bio oil yield by 20% or more due to, for example, the catalysts converting the protein, cellulose, and hemicellulose into oil.

Biofuels that are produced through hydrothermal liquefaction are carbon neutral in that there are no net carbon emissions produced when burning the biofuel. The algae used to produce the bio oils use photosynthesis to grow and, therefore, consume carbon dioxide from the ocean and/or atmosphere. The burning of the biofuels produced from algae or other plants releases carbon dioxide into the atmosphere. However, this is almost completely offset by the carbon dioxide consumed from growing the algae or plants. Furthermore, hydrothermal liquefaction is a clean process that does not produce harmful compounds, such as ammonia, NOx, or SOx. Instead, the heteroatoms, such as nitrogen, sulfur, and chlorine, are converted into harmless byproducts including $N_2$ and inorganic acids that can be neutralized with bases.

Figure 4:
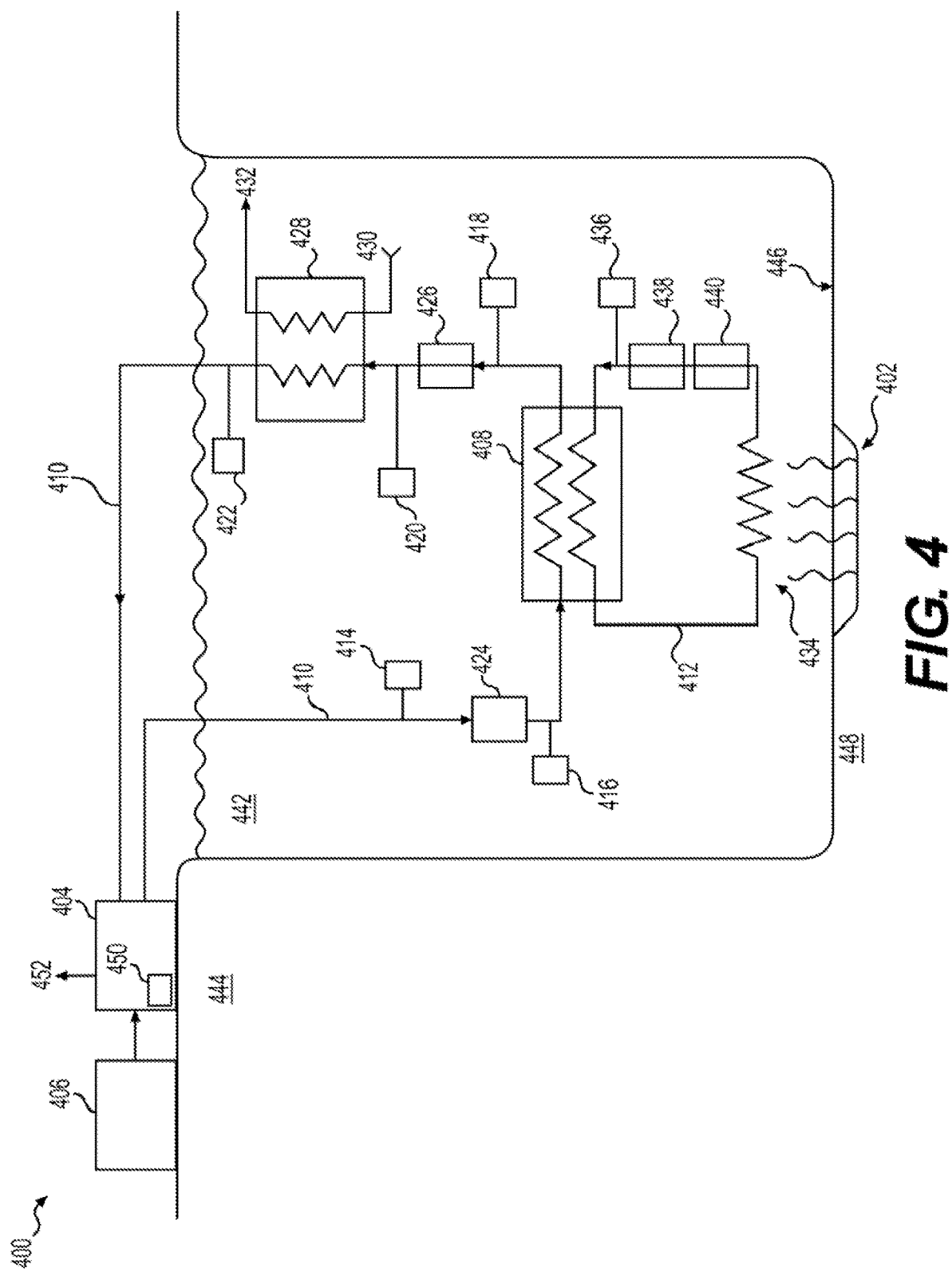
FIG. 4 shows another system for converting a biomass into biofuel using a geothermal heat source.

FIG. 4 shows system 400 for converting a biomass into biofuel using a geothermal heat source 402. System 400, however, uses a second conduit 412 and heat exchanger 434 to capture thermal energy from geothermal heat source 402. Conduit 412 uses a superheated fluid to transfer the thermal energy to HTL converter 408 to convert the biomass into a processed biomass, e.g., biofuel. By using a second conduit 412 and heat exchanger 434, system 400 is arranged to control the temperature within HTL converter 408 by controlling the temperature of the superheated fluid being transported to the HTL converter 408 within the second conduit 412. Controller 450 controls the temperature and/or flow rate of the superheated fluid within conduit 412 by controlling the operations of flow regulator 438 and temperature regulator 440. Flow regulator 438 may operate and have components similar to flow regulators 322 and 324. Temperature regulator 440 may include a heat exchanger and component like heat exchanger 326. Controller 450 may control the flow rate of cooling water through regulator 440 to control the temperature of the superheated fluid exiting regulator 440 that is then transported to HTL converter 408.

System 400 includes a biomass processing station 404 arranged to receive the biomass from a biomass harvester 406 and then output the biomass to HTL converter 408. The processing station 404 also receives a processed biomass from the HTL converter 408. The system 400 uses a first conduit 410 to transport the biomass from the biomass processing station 404 to the HTL converter 408 and transport the processed biomass from the HTL converter 408 to the biomass processing station 404. Biomass processing station 404 may output the processed biomass via outlet 452 to a storage facility and/or processing facility for further processing. HTL converter 408 includes a heat exchanger arranged to transfer thermal energy from the superheated fluid in conduit 412 to the biomass being transported through conduit 410 to convert the biomass into the processed biomass. The superheated fluid is heated by the geothermal heat source 402 via heat exchanger 434. Controller 450 is arranged to monitor one or more conditions of the biomass via sensors 414, 416, 418, 420, and 422 at the one or more locations along the conduit 410 and adjust operations of one or more components 422, 424, and 426 along the conduit 410 to, thereby, adjust the one or more conditions of the biomass at the one or more locations along the conduit 410.

The conditions monitored by sensors 414-422 may include, without limitation, temperature, rate of temperature change, pressure, flow rate, catalyst concentration, and/or residence time the biomass within HTL converter 408. Controller 450 may monitor the one or more conditions of the biomass by receiving sensor data associated with one or more conditions of the biomass from one or more of sensors 414-422. The biomass may include an algae while the processed biomass may include bio oil, bio crude, and/or biofuel. The conversion of the biomass to biofuel may include depolymerization of the biomass to bio oil.

In various implementations, controller 450 is configured to adjust the operations of one or more of components 424, 426, and 428 to optimize conditions of the biomass and, thereby, optimize a yield of the processed biomass. Components 424 and 426 may include flow regulators such as, for example, a pump and/or a flow control valve. A pump may be a variable speed pump to adjust flow rate within conduit 410. A flow control valve may be adjustable to adjust flow rate with conduit 410. Heat exchanger 428 may be controlled by controller 450 to regulate an output temperature of from heat exchanger 428 before the processed biomass, e.g., biofuel, is returned to processing station 404. Heat exchanger 428 may receive cooling water at a temperature set by the depth of water inlet 430 and pass water through to extract heat from the processed biomass also passing through heat exchanger 428 via conduit 410. The flow rate of cooling water through heat exchanger 428 may be regulated by a flow regulator controlled by controller 450. The heated cooling water is then expelled into the surround body of water 442, e.g., the ocean via outlet 432. In this way, the temperature of the processed biomass is reduced before handling at processing station 404. Although not shown in FIG. 4, controller 450 is in electrical communications, e.g., via electrical conduits, with sensors 414-422 and 436, and components 322-328, and 438-440 to enable electrical communications associated with controlling conditions of the biomass in system 400.

In various implementations, controller 450 monitors one or more conditions of the superheated fluid at one or more locations along the second conduit 412 via sensor 436 and adjusts operations of one or more components 438 and 440 along the second conduit 412 adjust the one or more conditions of the superheated fluid at the one or more locations along the second conduit 410. By adjusting the temperature of the superheated fluid in conduit 412, the temperature within HTL converter 408 can be set as desired to facilitate more efficient HTL conversion of the biomass to biofuel in conduit 410. One technical advantage of system 400 is that the temperature of the superheated fluid in the HTL converter 408 can be regulated in a more consistent manner regardless of possible fluctuations in thermal energy output from the geothermal heat source 402. Controller 450 may utilize an AI application and/or deep learning techniques described with respect to systems 200 and 300 to automatically control and optimize biofuel production within system 400.

As illustrated in FIG. 4, HTL converter 408 may reside within a body of water 442 such as the ocean where a substantial portion of conduit 410 is surrounded by the body of water 442. While FIG. 4 shows the harvester 406 and biomass processing station 404 on land 444, the biomass processing station 404 and biomass harvester 406 may reside in proximity with each other within the body of water 444. The biomass processing station 404 may be located on a vessel, rig, or platform on the body of water 442. The harvester 406 may include one or more photobioreactors or deepwater photobioreactors in the body of water 442 and in proximity to the system 400 and/or station 404. The harvester 406 may be less than or equal to about 5 miles (about 8 Km), 3 miles (about 4.8 Km), 1 mile (about 1.6 Km), 0.5 miles (about 0.8 Km), 0.25 miles (about 0.4 Km) from system 400 and/or biomass processing station 404.

Although heat exchanger 434 is shown adjacent to geothermal heat source 402, heat exchanger 434 may extend through source 402 within the earth 448 below the ocean floor 446. Heat exchanger 434 may include a section of conduit 412 that extends through and/or near source 402. The location of heat exchanger 434 with respect to source 402 may depend on the desired amount of heat exchange and temperature needed to convert the biomass into a processed biomass. Heat exchanger 434 may include a single pipe (i.e., section of conduit 412) that extends through a region of the geothermal heat source 402. The pipe may be substantially straight, U-shaped, serpentine, and/or curved in portions. Heat exchanger 434 may include multiple parallel pipes and/or capillaries with a common inlet and outlet that interface with conduit 412. Conduit 410 and/or conduit 412 may have one or more sections of pipe including at least one of Tungsten and Titanium.

In some implementations, system 400 may interface with geothermal sources emitting temperatures up to 900 C. Conduit 412 may use much larger diameter pipes than the traditional 200 mm used from oil drilling equipment. In one implementation, the superheated fluid includes a supercritical $CO_2$ (SCCO2) fluid. Supercritical $CO_2$ has properties between a gas and a liquid. While it still flows like a liquid when under pressures of 100 atmospheres or more, the volumetric density is inversely proportional to temperature so it can act like a liquid but be one tenth the density. The lower temperatures of traditional and enhanced geothermal systems operate at around 200 C to 300 C, and the complexity of these traditional systems have reduced their practicality. In some implementations, system 400 uses a higher temperature fluid in conduit 412 including, for example, a SCCO2 fluid, which provides for more efficient high temperature geothermal operations and biomass conversion. In some implementations, a volumetric density change of the SCCO2 fluid means the flow rate in conduit 412 has to maintain mass flow, which at 50 C and 200 Bar is about 0.7844 g/cc and at 550 C is 0.1244 g/cc.

Figure 5:
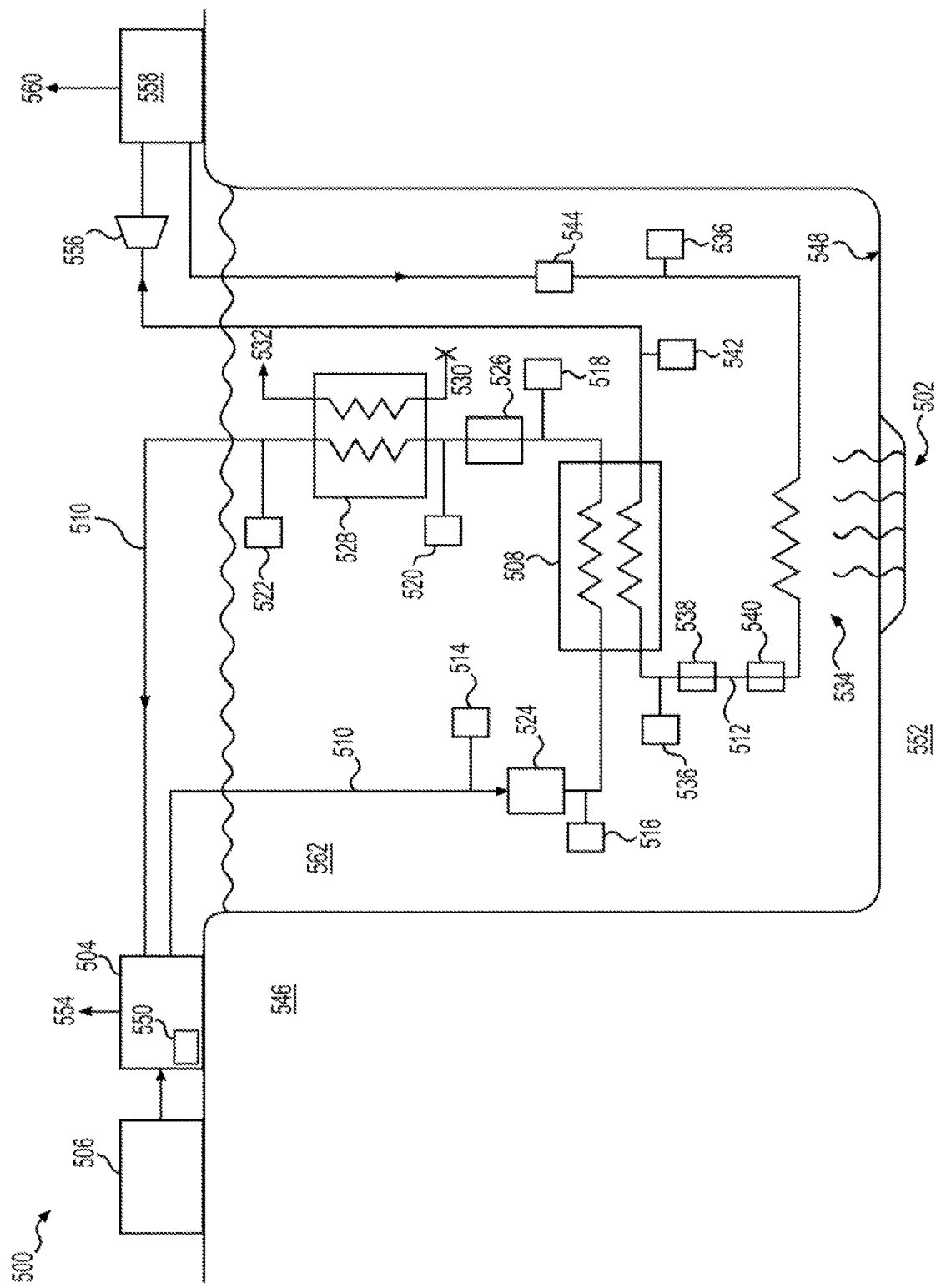
FIG. 5 shows a further system for converting a biomass into biofuel using a geothermal heat source.

FIG. 5 shows a system 500 for converting a biomass into biofuel and for generating electrical power using a geothermal heat source 502. In addition to including a biomass processing station 504, system 500 includes a power turbine 556 and generator 558 configured to output electrical power via power outlet 560. The power generated via generator 558 may be used to provide power to external loads and/or may be used to power one or more components of system 500.

System 500 includes a biomass processing station 504 arranged to receive the biomass from a biomass harvester 506 and then output the biomass to HTL converter 508. The processing station 504 also receives a processed biomass from the HTL converter 508. The system 500 uses a first conduit 510 to transport the biomass from the biomass processing station 504 to the HTL converter 508 and transport the processed biomass from the HTL converter 508 to the biomass processing station 504. Biomass processing station 504 may output the processed biomass via outlet 554 to a storage facility and/or processing facility for further processing. HTL converter 508 includes a heat exchanger arranged to transfer thermal energy from superheated fluid in conduit 512 to the biomass being transported through conduit 510 to convert the biomass into the processed biomass. The superheated fluid is heated by the geothermal heat source 502 via heat exchanger 534. Controller 550 is arranged to monitor one or more conditions of the biomass via sensors 514, 516, 518, 520, and 522 at the one or more locations along the conduit 510 and adjust operations of one or more components 522, 524, and 526 along the conduit 510 to, thereby, adjust the one or more conditions of the biomass at the one or more locations along the conduit 510.

The conditions monitored by sensors 514-522 may include, without limitation, temperature, rate of temperature change, pressure, flow rate, catalyst concentration, and/or residence time the biomass within HTL converter 508. Controller 550 may monitor the one or more conditions of the biomass by receiving sensor data associated with one or more conditions of the biomass from one or more sensors 514-522. The biomass may include an algae while the processed biomass may include bio oil, bio crude, and/or biofuel. The conversion of the biomass to biofuel may include depolymerization of the biomass to bio oil.

In various implementations, controller 550 is configured to adjust the operations of one or more of components 524, 526, and 528 to optimize conditions of the biomass and, thereby, optimize a yield of the processed biomass. Components 524 and 526 may include flow regulators such as, for example, a pump and/or a flow control valve. A pump may be a variable speed pump to adjust flow rate within conduit 510. A flow control valve may be adjustable to adjust flow rate with conduit 510. Heat exchanger 528 may be controlled by controller 550 to regulate an output temperature of from heat exchanger 528 before the processed biomass, e.g., biofuel, is returned to processing station 504. Heat exchanger 528 may receive cooling water at a temperature set by the depth of water inlet 530 and pass water through to extract heat from the processed biomass also passing through heat exchanger 528 via conduit 510. The flow rate of cooling water through heat exchanger 528 may be regulated by a flow regulator controlled by controller 550. The heated cooling water is then expelled into the surround body of water 562, e.g., the ocean via outlet 532. In this way, the temperature of the processed biomass is reduced before handling at processing station 504. Although not shown in FIG. 5, controller 550 is in electrical communications, e.g., via electrical conduits, with sensors 514-522, 536, and 542, and components 522-528 and 538-540 to enable electrical communications associated with controlling conditions of the biomass in system 500.

In various implementations, controller 550 monitors one or more conditions of the superheated fluid at one or more locations along the second conduit 512, via sensors 536 and 542, and adjusts operations of one or more components 538 and 540 along the second conduit 512 adjust the one or more conditions of the superheated fluid at the one or more locations along the second conduit 510. By adjusting the temperature of the superheated fluid in conduit 512, the temperature within HTL converter 508 can be set as desired to facilitate more efficient HTL conversion of the biomass to biofuel in conduit 510. One technical advantage of system 500 is that the temperature of the superheated fluid in the HTL converter 508 can be regulated in a more consistent manner regardless of possible fluctuations in thermal energy output from the geothermal heat source 502. Controller 550 may utilize AI applications and/or deep learning techniques described with respect to systems 200 and 300 to automatically control and optimize biofuel production within system 500. The superheated fluid within conduit 512 may also be used to drive turbine 556 which, in turn, drives a rotor with generator 558 to produce electrical power.

As illustrated in FIG. 5, HTL converter 508 may reside within a body of water 562 such as the ocean where a substantial portion of conduit 510 is surrounded by the body of water 562. While FIG. 5 shows the harvester 506 and biomass processing station 504 on land 546, the biomass processing station 504 and biomass harvester 506 may reside in proximity with each other within the body of water 562. The biomass processing station 504 may be located on a vessel, rig, or platform on the body of water 562. The harvester 506 may include one or more photobioreactors or deepwater photobioreactors in the body of water 562 and in proximity to the system 500 and/or station 504. The harvester 506 may be less than or equal to about 5 miles (about 8 Km), 3 miles (about 4.8 Km), 1 mile (about 1.6 Km), 0.5 miles (about 0.8 Km), 0.25 miles (about 0.4 Km) from system 500 and/or biomass processing station 504.

Although heat exchanger 534 is shown adjacent to geothermal heat source 502, heat exchanger 534 may extend through source 502 within the earth 552 below the ocean floor 548. Heat exchanger 534 may include a section of conduit 512 that extends through and/or near source 502. The location of heat exchanger 534 with respect to source 502 may depend on the desired amount of heat exchange and temperature needed to convert the biomass into a processed biomass. Heat exchanger 534 may include a single pipe (i.e., section of conduit 512) that extends through a region of the geothermal heat source 502. The pipe may be substantially straight, U-shaped, serpentine, and/or curved in portions. Heat exchanger 534 may include multiple parallel pipes and/or capillaries with a common inlet and outlet that interface with conduit 512. Conduit 510 and/or conduit 512 may have one or more sections of pipe including at least one of Tungsten and Titanium.

In some implementations, system 500 may interface with geothermal sources emitting temperatures up to 900 C. Conduit 512 may use much larger diameter pipes than the traditional 200 mm used from oil drilling equipment. In one implementation, the superheated fluid includes a supercritical CO2 (SCCO2) fluid. Supercritical CO2 has properties between a gas and a liquid. While it still flows like a liquid when under pressures of 100 atmospheres or more, the volumetric density is inversely proportional to temperature so it can act like a liquid but be one tenth the density. The lower temperatures of traditional and enhanced geothermal systems operate at around 200 C to 300 C, and the complexity of these traditional systems have reduced their practicality. In some implementations, system 500 uses a higher temperature fluid in conduit 512 including, for example, a SCCO2 fluid, which provides for more efficient high temperature geothermal operations and biomass conversion. In some implementations, a volumetric density change of the SCCO2 fluid means the flow rate in conduit 512 has to maintain mass flow, which at 50 C and 200 Bar is about 0.7844 g/cc and at 550 C is 0.1244 g/cc.

Figure 6:
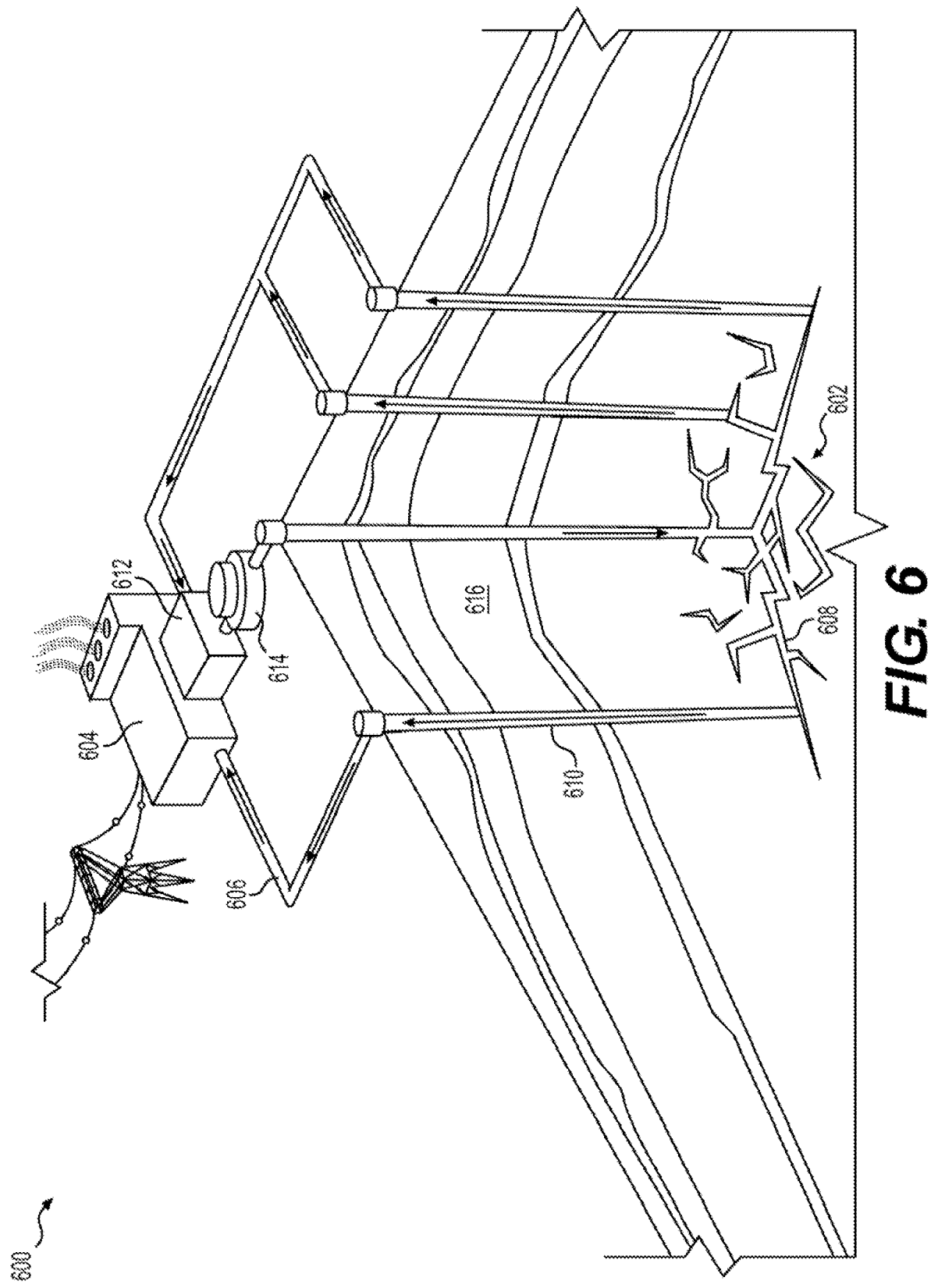
FIG. 6 shows a land-based system for converting a biomass into biofuel using a geothermal heat source.

FIG. 6 shows a cut-out view of a land-based system 600 for converting a biomass into biofuel using a geothermal heat source 602. System 600 includes a biomass processing station 604 arranged to receive the biomass from a biomass harvester 606 and then output the biomass to a HTL converter 608 within the earth 616. The processing station 604 also receives a processed biomass from the HTL converter 608. The system 600 uses a conduit 610 to transport the biomass from the biomass processing station 604 to the HTL converter 608 and transport the processed biomass from the HTL converter 608 to the biomass processing station 604. HTL converter 608 may include a heat exchanger including, for example, a section of conduit 610, that is arranged to transfer thermal energy from geothermal heat source 602 to the biomass being transported through conduit 610 to convert the biomass into a processed biomass. System 600 also includes a controller 612 that is arranged to monitor one or more conditions of the biomass via sensors at the one or more locations along the conduit 610 and adjust operations of one or more components along the conduit 610 to, thereby, adjust the one or more conditions of the biomass at the one or more locations along the conduit 610. The sensors and components of system 600 may be configured and/or operate in a similar manner as the sensors and components described with respect to systems 300, 400, and 500. In some implementations, some of the sensors and/or components may reside in the biomass processing station 604. Biomass processing station may output and store processed biomass, e.g., biofuel, in a storage tank and/or reservoir 614.

FIG. 7 shows a process 700 for converting a biomass into biofuel using a geothermal heat source, such as heat source 302, 402, and 502. Process 700 includes: receiving, at a biomass processing station, the biomass from a biomass harvester (Step 702); transporting the biomass from the biomass processing station to a hydrothermal HTL converter via a conduit where the HTL converter is located remotely from the biomass processing station and within proximity to a geothermal heat source (704); transferring thermal energy from the geothermal heat source to the biomass to convert the biomass into a processed biomass (706); monitoring one or more conditions of the biomass at one or more locations along the conduit (708); adjusting operations of one or more components along the conduit, in response to the monitored conditions, to adjust the one or more conditions of the biomass at the one or more locations along the conduit (710); and receiving, at the biomass processing station, the processed biomass from the HTL converter via the conduit (712).

Elements or steps of different implementations described may be combined to form other implementations not specifically set forth previously. Elements or steps may be left out of the systems or processes described previously without adversely affecting their operation or the operation of the system in general. Furthermore, various separate elements or steps may be combined into one or more individual elements or steps to perform the functions described in this specification.

Other implementations not specifically described in this specification are also within the scope of the following claims.

What is claimed is:

1. A method for converting a biomass into a biofuel comprising:
   receiving, at a biomass processing station, the biomass from a biomass harvester;
   transporting the biomass from the biomass processing station to a hydrothermal liquefaction (HTL) converter via a conduit, the HTL converter being located remotely from the biomass processing station and within proximity to a geothermal heat source, wherein a portion of the conduit is located below the surface of an ocean;
   transferring thermal energy from the geothermal heat source to the biomass to convert the biomass into a processed biomass, wherein the geothermal heat source is located below the surface of the ocean;
   monitoring, via one or more sensors at one or more locations along the conduit, one or more conditions of the biomass at the one or more locations along the conduit;
   adjusting operations of one or more components along the conduit to adjust the one or more conditions of the biomass at the one or more locations along the conduit; and
   receiving, at the biomass processing station, the processed biomass from the HTL converter via the conduit.

2. The method of claim 1 comprising controlling, by a controller, the one or more conditions of the biomass by receiving sensor data from the one or more sensors associated with the one or more conditions of the biomass from the one or more sensors.

3. The method of claim 1, wherein the biomass includes an algae and the processed biomass includes bio oil, and wherein converting the biomass includes depolymerization of the biomass to bio oil.

4. The method of claim 1 comprising adjusting the operations of the one or more components to optimize the one or more conditions of the biomass to, thereby, optimize a production yield of the processed biomass.

5. The method of claim 1, wherein the one or more components include at least one of a pump and a flow control valve.

6. The method of claim 1, wherein the one or more conditions of the biomass include at least one of temperature, pressure, flow rate, catalyst concentration, and residence time within the HTL converter.

7. The method of claim 1, wherein the geothermal heat source includes at least one of a volcano, volcanic vent, and a hydrothermal vent.

8. The method of claim 1 comprising positioning the HTL converter within the ocean.

9. The method of claim 8 comprising positioning a substantial portion of the conduit within the ocean.

* * * * *